United States Patent [19]

Chao et al.

[11] 4,394,178

[45] Jul. 19, 1983

[54] BULK LACTULOSE/LACTOSE SEPARATION BY SELECTIVE ADSORPTION ON ZEOLITIC MOLECULAR SIEVES

[75] Inventors: Chien C. Chao, Millwood; John D. Sherman, Chappaqua, both of N.Y.

[73] Assignee: Union Carbide Corporation, Danbury, Conn.

[21] Appl. No.: 329,501

[22] Filed: Dec. 10, 1981

[51] Int. Cl.[3] .......................... C13D 3/12; C07H 1/06

[52] U.S. Cl. .................................... 127/46.3; 127/55; 536/127; 252/455 Z; 210/691

[58] Field of Search ....................... 127/46.3, 46.2, 55; 536/1.1, 127; 252/455 Z; 210/691, 673, 674

[56] References Cited

U.S. PATENT DOCUMENTS

| | | | |
|---|---|---|---|
| 3,816,174 | 6/1974 | Nagasawa et al. | 536/1.1 |
| 4,157,267 | 6/1979 | Odawara et al. | 127/46.2 |
| 4,340,724 | 7/1982 | Neuzil et al. | 127/46.3 X |

FOREIGN PATENT DOCUMENTS

| | | | |
|---|---|---|---|
| 52-71409 | 6/1977 | Japan | 210/691 |
| 1506429 | 4/1978 | United Kingdom . | |

OTHER PUBLICATIONS

Whistler et al., Methods in Carbohydrate Chemistry, vol. 1, Analysis & Preparation of Sugars; Academic Press, N.Y., 1962; pp. 325-328.

*Primary Examiner*—Kenneth M. Schor
*Attorney, Agent, or Firm*—Gary L. Wamer

[57] ABSTRACT

Lactulose is selectively adsorbed from admixture with lactose using specific cationic forms (particularly barium or potassium) of modified zeolite Y.

5 Claims, 5 Drawing Figures

BULK LACTULOSE/LACTOSE SEPARATION BY SELECTIVE ADSORPTION ON ZEOLITIC MOLECULAR SIEVES

The present invention relates to the liquid phase separation of mixtures of lactulose and lactose. More particularly, it relates to such a separation by selective adsorption on certain types of zeolite molecular sieves.

Lactulose is a disaccharide sugar constituted of galactose and fructose which has properties of considerable interest in the medical and food industries. It may be formed by converting lactose, another disaccharide, to lactulose by isomerization.

Lactose is a disaccharide formed by linking two six-carbon sugars, glucose and galactose. Lactose can be converted into lactulose by catalysis by bases, alkali or alkaline earth borates or aluminates, ion exchange resins, or enzymes. Because the reaction is usually incomplete, the reaction products are mixtures of lactose and lactulose. For many medical or food industry uses, the lactulose must be separated from such mixtures.

There is one diclosed method to separate lactose and lactulose using selective adsorption: Japanese Kokai No. 77-71409 (Odawara). Odawara teaches the use of an X- or Y-type zeolite substituted with alkaline earth metal ions (preferably calcium, strontium or barium) to separate the components of the mixture. Barium-substituted Type X (BaX) zeolite adsorbs neither lactulose nor lactose significantly. Calcium-substituted Type Y zeolite does not adsorb lactulose particularly strongly. As a result, the calcium-substituted Type Y zeolite is not particularly effective in separating the two sugars in that much of the lactulose contains quantities of lactose, rendering it impure. In the case of barium-substituted Type Y zeolite, the rate of approach to adsorption equilibrium is very slow, requiring a low process flow rate (approximately 0.072 $gpm/ft^2$). At such a low flow rate, the adsorption/desorption cycle time is very long. Thus, the capital investment for the separation process is not efficiently utilized. Another disadvantage to using barium-substituted Y-type zeolite (hereinafter referred to as "BaY") is the presence of barium ions on the zeolite. Although the feed solution containing lactose and lactulose may also contain a variety of cations, it is unlikely that barium ions will be among them. Therefore, as the feedstock travels through the zeolite, the barium ions will tend to be lost from the zeolite and leach into the product stream. This would, in turn require removal of barium ions from the product as well as either adding them to the feed stream in order to prevent loss of barium ions from the zeolite or periodic addition of ions to the zeolite to replenish the supply on the zeolite.

Since the sugar adsorption is cation-specific, it might be expected that a zeolite containing a larger number of cations would exhibit stronger affinity for adsorbates than a zeolite with a smaller number of cations. It is also expected that zeolites with stronger affinity for sugars would have poor counterdiffusion rates (see Table I for retention volumes which reflect adsorption affinities of zeolites.)

It has been discovered that potassium-exchanged zeolites with framework structures similar to that of the Y-type zeolite, but with much lower ion concentrations than either X- or Y-type zeolites (i.e., "modified Type Y zeolite"), separate lactose and lactulose better than KY. Furthermore, the barium form of this modified Y-type zeolite not only provides longer retention times than conventional barium-exchanged Y-type zeolites, but also unexpectedly exhibited greatly improved rates of adsorption and desorption.

DESCRIPTION OF THE INVENTION

Figure 1:
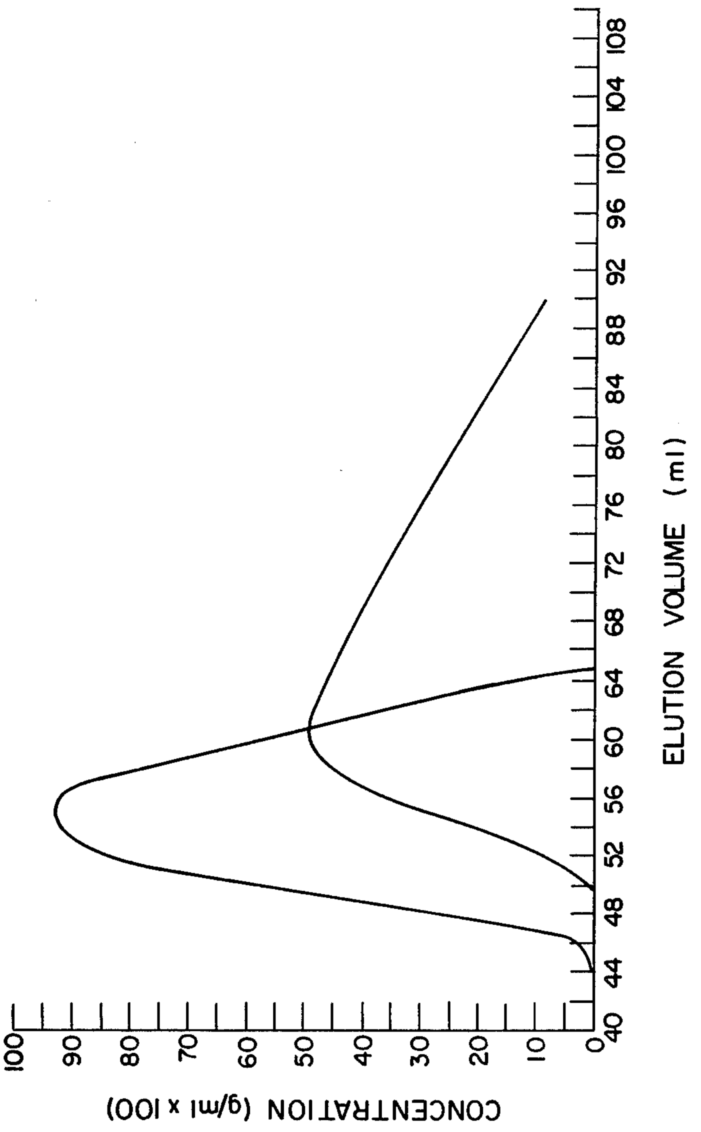
FIG. 1 shows the separation of lactose and lactulose by a conventional Type-Y zeolite which has been barium-exchanged.

The present invention comprises a process for separating lactulose from admixture with lactose by selective adsorption which comprises contacting a mixture comprising said compounds at a temperature of from 30° C. to 100° C. and at a pressure sufficient to maintain the system in the liquid phase with an adsorbent composition comprising at least one crystalline aluminosilicate zeolite selected from a group consisting of modified Type Y zeolite having a cation site concentration of from about 40 to about 10 equivalents per mole unit cell and a face centered cubic unit cell having an $a_o$ (for the decationized form; e.g., after steaming and before further cation exchange) of from 24.3 to 24.6 A, in which the zeolitic cations are more than 50% barium or potassium, whereby lactulose is selectively adsorbed thereon; removing the non-adsorbed portion of said mixture from contact with the zeolite adsorbent; and desorbing the lactulose therefrom by contacting said adsorbent with a desorbing agent and removing the desorbed lactulose.

Zeolite Y and the method for its manufacture are described in detail in U.S. Pat. No. 3,130,007, issued Apr. 21, 1964 to D. W. Breck. It is preferred that the modified Type Y zeolite be prepared in accordance with the method disclosed in British Pat. No. 1,506,429, published Apr. 5, 1978. This process comprises heating an ammonium-exchanged Type Y zeolite at a temperature between 550° and 800° C. for a period of at least 0.25 hours in pure steam or an inert atmosphere comprising a substantial amount of steam (at least 2 psia and preferably 1 atm of steam), removing at least a major proportion, preferably all, of any ammonia generated by the heated zeolite from contact with the zeolite, and cooling the steamed zeolite to a temperature below 350° C. and preferably below 300° C. The final product can be characterized by $a_o$ values (for the decationized form; e.g., after steaming and before further cation exchange) between about 24.3 and about 24.6 A and cation concentrations of from 40 to 10 equivalents per mole unit cell.

It is believed that steaming causes an alteration of the zeolite framework so as to reduce the framework aluminum content with a concommitant decrease in cation exchange capacity. Therefore, it is expected that, while the steaming method is preferred, other methods for modifying Type Y zeolites so as to reduce cation exchange capacity will produce zeolites with separation capabilities similar to those of the steamed zeolites.

The adsorption affinities of various zeolites for sugars was determined by a "pulse test". This test consisted of packing a column with the appropriate zeolite, placing it in a block heater to maintain constant temperature, and eluting solutions through the column to determine retention volume of solute. The retention volume of solute is defined as elution volume of solute minus "void volume". "Void volume" is the volume of solvent needed to elute a non-sorbing solute through the column. A soluble polymer of fructose, inulin, which is too large to be sorbed into the zeolite pores, was chosen as the solute to determine void volume. The elution volume of inulin was first determined. The elution volumes of sugars were then determined under similar experimental conditions. The retention volumes were calculated and are recorded in Table I, below. From the retention volume data, the separation factor (S.F.), ($\alpha$ lactulose)/(lactose), was calculated in accordance with the following equation:

$$S.F. = \alpha(\text{lactulose/lactose}) = \frac{(\text{retention volume for lactulose peak})}{(\text{retention volume for lactose peak})}$$

An $\alpha$ value greater than unity indicates that the particular adsorbent was lactulose-selective. The separation factor values calculated according to the above-mentioned method are found in Table II. It is apparent from Table II that the barium- and potassium-substituted modified Zeolite Y are lactulose-selective. Barium-substituted conventional zeolite X and potassium substituted conventional zeolite Y provided no separation whatsoever.

TABLE I

RETENTION VOLUME OF SUGARS (in ml)

Flow Rate: 1 ml/min.
Temp: 70° C.
Elution peak was detected by differential refractometer
Column Dimension: 40 cm × 0.77 cm (ID)

| Zeolite | Inulin | Lactose | Lactulose |
|---|---|---|---|
| BaX | 0 | 0.04 | 0 |
| BaY | 0 | 1.7 | 3.1 |
| BaSY | 0 | 3.5 | 5.8 |
| KY | 0 | 2.0 | 2.0 |
| KSY | 0 | 2.3 | 3.5 |

TABLE II

SEPARATION FACTORS FOR LACTULOSE/LACTOSE SEPARATION

| ZEOLITE | $\alpha$ LACTULOSE/LACTOSE |
|---|---|
| BaX | 1.0 |
| BaY | 1.82 |
| BaSY | 1.66 |
| KY | 1.00 |
| KSY | 1.52 |

Figure 2:
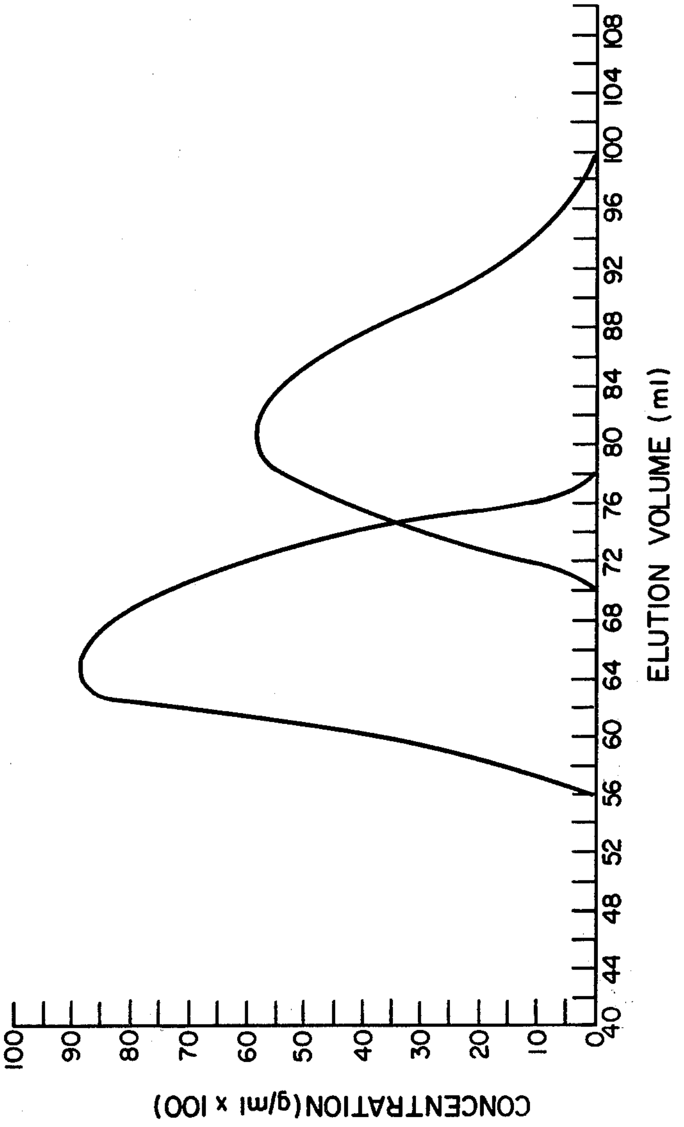
FIG. 2 shows the separation of lactose and lactulose by a steam-modified Type-Y zeolite which has been barium-exchanged.

Another parameter which is important in determining the overall separation efficiency of the zeolite used in the process of this invention is the "R-factor". This factor is often used to determine separation efficiency because it takes into account the rate of diffusion through the zeolite as well as selectivity, or adsorption affinity. The R-factor is defined as follows:

$$2 \times \frac{(\text{Retention volume of lactulose} - \text{Retention volume of lactose})}{(\text{Peak width of lactulose peak} + \text{Peak width of lactose peak})}$$

where the peak width is measured at half-height of the peaks of elution curves which measure concentration versus elution volume. Referring to FIG. 1, the calculated R-factor is 0.34 for barium-substituted zeolite Type Y. In comparison, the calculated R-factor for barium-substituted modified zeolite Type Y, as determined from FIG. 2, is 1.14. Thus it can be seen that the modified zeolite has superior overall separation characteristics, despite its stronger affinity for lactose and lactulose.

In separating lactulose and lactose in the present process, a bed of solid zeolite adsorbent is contacted with a feed mixture, the lactulose is preferentially adsorbed on the adsorbent, the unadsorbed or raffinate mixture is removed from the adsorbent bed, and the adsorbed lactulose is desorbed from the zeolite adsorbent. The adsorbent can, if desired, be contained in a single bed, a plurality of beds in which conventional swing-bed operation techniques are utilized, or a simulated moving-bed countercurrent type of apparatus. The preferred mode of operation is the simulated moving-bed technique such as that described in U.S. Pat. No. 2,985,589 issued May 23, 1961 to D. B. Broughton et al. In this method of operation, the selection of a suitable displacing or desorbing agent or fluid (solvent) must take into account the requirements that it be capable of readily displacing absorbed lactulose from the adsorbent bed and also that lactulose from the feed mixture be able to displace adsorbed desorbing agent from a previous desorption step. Further, the desorbing agent employed should be readily separable from admixture with the sugar components of the feedstock. Therefore it is contemplated that a desorbing agent having characteristics which allow it to be easily fractionated from the sugars should be used. For example, volatile desorbing agents should be used, such as alcohols, ketones, admixtures of alcohols and water, particularly methanol and ethanol. The most preferred desorbing agent which can be used in the present process is water.

Of the particular above-enumerated zeolites, barium-substituted modified zeolite Y (BaSY) is found to be most advantageous in this process. It has been found to have high selectivity for lactulose and to impart no serious rate (diffusion) or catalytic problems to the separation process. Also preferred is the use of potassium-substituted modified zeolite Y (KSY). Potassium salts may be used as catalysts in the conversion of lactose to lactulose and therefore may be present in the feedstock. If a potassium-substituted zeolite is used for separation, the potassium ions will not leach into the product during the process. This eliminates the need for regeneration of the zeolite.

While it is possible to utilize the activated adsorbent zeolite crystals in a non-agglomerated form, it is generally more feasible, particularly when the process involves the use of a fixed adsorption bed, to agglomerate the crystals into larger particles to decrease the pressure drop in the system. The particular agglomerating agent and the agglomeration procedure employed are not critical factors, but it is important that the bonding agent be as inert toward the lactulose, lactose and the desorbing agent as possible. The proportions of zeolite and binder are advantageously in the range of 4 to 20 parts zeolite per part binder on an anhydrous weight basis.

The temperature at which the adsorption step of the process should be carried out should be from about 30° C. to about 100° C. It has been found that at temperatures below about 30° C. the counter-diffusion rate between lactulose and lactose is too slow, i.e., a sufficient selectivity for the lactulose is not exhibited by the zeolite. Above about 100° C. the sugars tend to degrade. Preferably, the adsorption step should take place between about 60° C. and about 80° C. Pressure conditions must be maintained so as to keep the system in liquid phase. Thus, higher process temperatures needlessly necessitate high pressure apparatus and increase the cost of the process.

Figure 5:
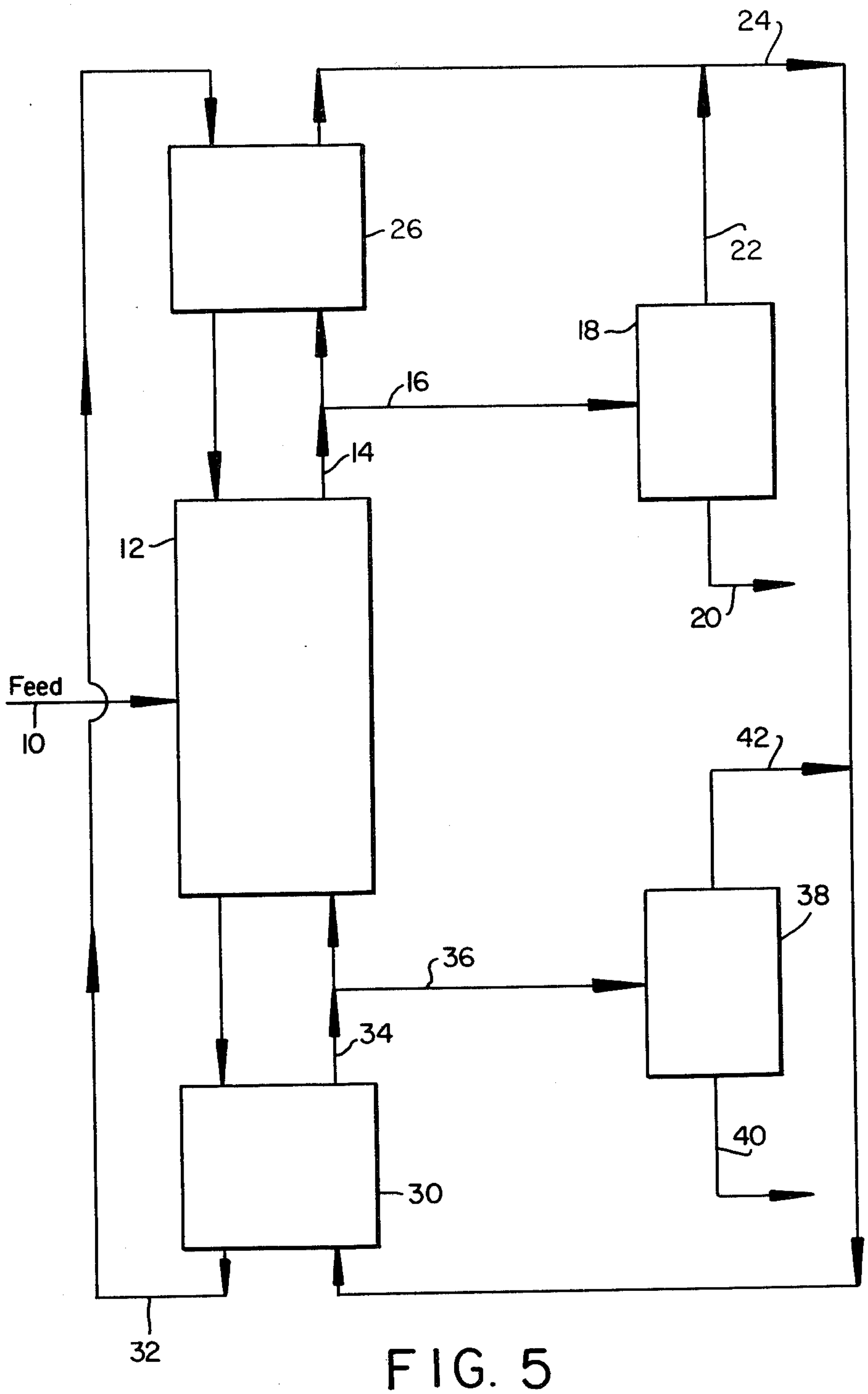
FIG. 5 represents one typical embodiment of the process of the present invention.

In the drawings FIG. 5 represents a hypothetical moving-bed countercurrent flow diagram involved in carrying out a typical process embodiment of the present invention.

With reference to the drawing, it will be understood that whereas the liquid stream inlets and outlets are represented as being fixed, and the adsorbent mass is represented as moving with respect to the counterflow of feedstock and desorbing material, this representation is intended primarily to facilitate describing the functioning of the system. In practice the sorbent mass would ordinarily be in a fixed bed with the liquid stream inlets and outlets moving with respect thereto. Accordingly, a feedstock consisting essentially of a mixture of 10 weight percent lactulose and 24 weight-percent lactose is fed into the system through line 10 to adsorbent bed 12 which contains particles of activated zeolite KSY or BaSY adsorbent in transit downwardly therethrough. The temperature is at 70° C. throughout the entire system and the pressure is substantially atmospheric. The lactulose component of the feedstock is adsorbed preferentially on the zeolite particles moving through bed 12, and the raffinate lactose is entrained in the liquid stream of water desorbing agent which flows upwardly through bed 12. This liquid mixture of the lactose component and the desorbing agent leave bed 12 through line 14 and a major portion thereof is withdrawn through line 16 and fed into evaporation apparatus 18 wherein the mixture is fractionated and the concentrated lactose is discharged through line 20 to be recycled to the isomerization reactor. The water desorbing agent leaves the evaporation apparatus 18 through line 22 and is fed to line 24 through which it is admixed with additional desorbing agent leaving the adsorbent bed 26, and is recycled to the bottom of adsorbent bed 30. The zeolite KSY or BaSY carrying adsorbed lactulose passes downward through line into bed 30 where it is counter-currently contacted with recycled desorbing agent which effectively desorbs the lactulose therefrom before the adsorbent passes through bed 30 and enters line 32 through which it is recycled to the top of adsorbent bed 26. The desorbing agent and desorbed lactulose leave 30 through line 34. A portion of this liquid mixture is diverted through line 36, where it passes evaporation apparatus 38, and the remaining portion passes upward through adsorbent bed 12 for further treatment as hereinbefore described. In evaporation apparatus 38, the desorbing agent and lactulose are fractionated. The lactulose product is recovered through line 40 and the desorbing agent is either disposed of or passes through line 42 into line 24 for recycle as described above. The undiverted portion of the desorbing agent/lactose mixture passes from bed 12 through line 14 enters bed 26 and moves counter-currently upward therethrough with respect to the desorbing agent laden zeolite adsorbent passing downwardly therethrough from recycle line 32. The desorbing agent passes from bed 26 in a relatively pure form through recycle line 24 and to bed 30 as hereinbefore described.

The following examples are illustrative of the practice of this invention. However, they do not serve to limit the invention to the embodiments in the Examples.

As used in the Examples appearing below the following abbreviations and symbols have the indicated meaning:

BaY . . . barium-exchanged conventional zeolite Y
BaSY . . . barium-exchanged steam-modified zeolite Y
$gpm/ft^2$ . . . gallons per minute per square foot
KSY . . . potassium-exchanged steam-modified zeolite Y

EXAMPLE 1

A 1.6 meter column having an inside diameter of 0.77 cm was filled with 30×50 mesh barium-exchanged conventional zeolite Y bonded with 20% binder. The column was filled with water and flow rate through the column of 0.53 $gpm/ft^2$ was maintained. The column was held at a temperature of 160° F. For a period of two minutes a solution containing 5 weight percent lactose and 5 weight percent lactulose ("feed pulse") was substituted for the water stream and then the water stream containing no dissolved sugars was reestablished. The composition of the effluent stream from the column was determined by collecting samples and analyzing samples over time with a liquid chromatograph. The elution curves of the sugars are given in FIG. 1. At this flow rate, BaY cannot separate lactulose from lactose with efficiency.

EXAMPLE 2

The same column and experimental procedures used in Example 1 were used. However, instead of using 30×50 mesh BaY, 30×50 mesh BaSY bonded with 20% binder was used. The elution curves given in FIG. 2 demonstrate that BaSY can efficiently separate lactulose from lactose.

EXAMPLE 3

Figure 3:
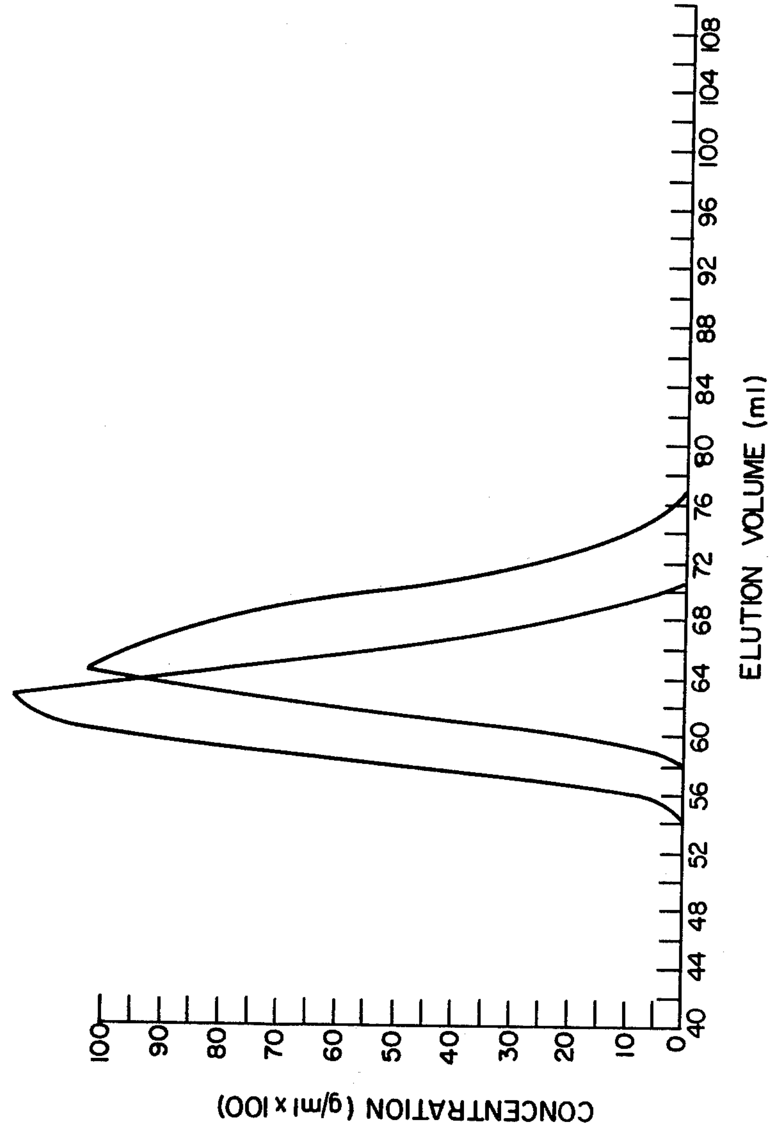
FIGS. 3 and 4 show separations of lactose and lactulose using steam-modified zeolite Type Y which has been potassium-exchanged.

The same column and experimental procedures used in Example 1 were used. However, instead of using 30×50 mesh BaY, 30×50 mesh KSY bonded with 20% binder was used. The elution curves given in FIG. 3 indicate that KSY can also separate lactulose from lactose.

EXAMPLE 4

Figure 4:
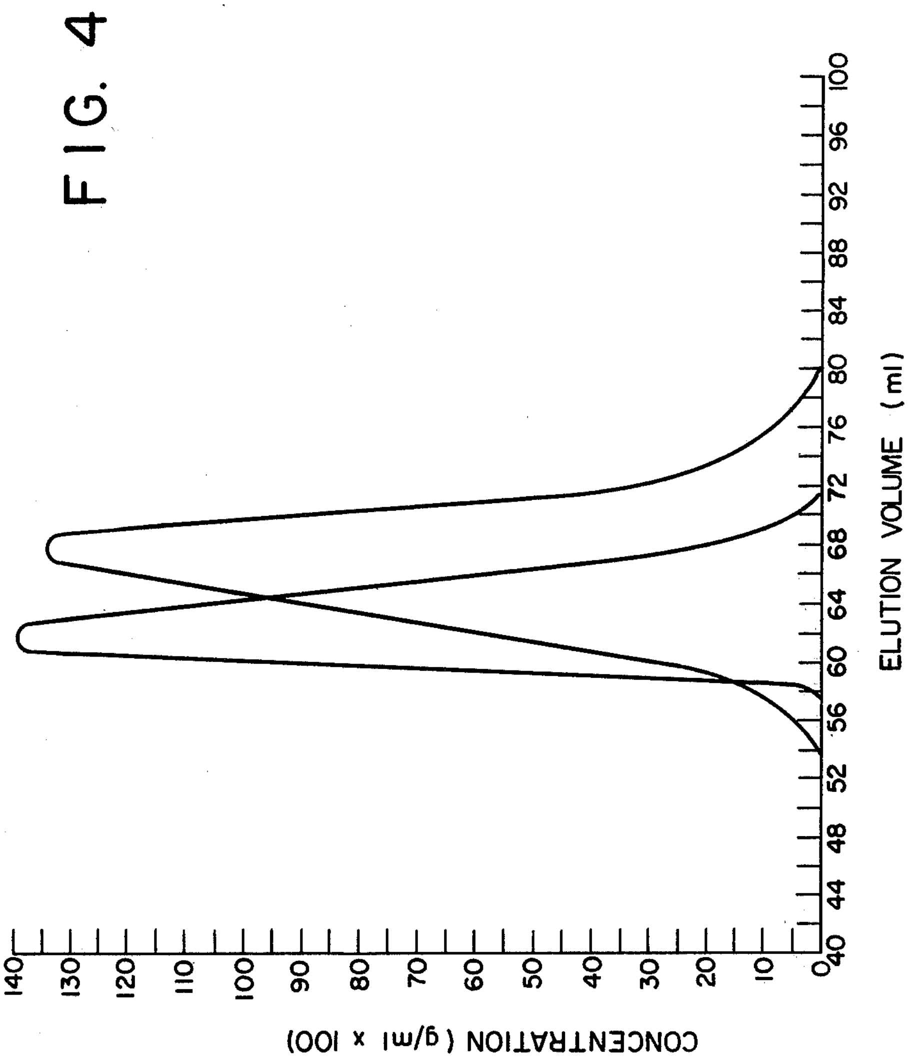

The same column, experimental procedures and zeolite used in Example 3 were used. However, the feed pulse contained 5 weight % lactulose and 5% lactose. The elution curves are given in FIG. 4.

What is claimed is:

1. A process for separating lactulose from admixture with lactose by selective adsorption which comprises contacting a mixture comprising said compounds at a temperature of from 30° C. to 100° C. and at a pressure sufficient to maintain the system in the liquid phase with an adsorbent composition comprising at least one crystalline aluminosilicate zeolite selected from a group consisting of modified zeolite Type Y having a cation site concentration of from about 40 to about 10 equivalents per mole unit cell and a face centered cubic unit cell having an $a_o$ for the decationized form of from 24.3 to 24.6 Å in which the zeolitic cations are more than 50% barium or potassium, whereby lactulose is selectively adsorbed thereon; removing the nonadsorbed portion of said mixture from contact with the zeolite adsorbent; and desorbing the lactulose therefrom by contacting said adsorbent with a desorbing agent and removing the desorbed lactulose.

2. A process in accordance with claim 1 wherein the temperature is from about 60° C. to about 80° C.

3. A process in accordance with claim 1 wherein the desorbent is selected from the group consisting of methanol, ethanol, water and mixtures of methanol, ethanol and water.

4. A process in accordance with claim 1 wherein the desorbent is water.

5. A process for separating lactulose from admixture with lactose by selective adsorption which comprises contacting a mixture comprising said compounds at a temperature of from 30° C. to 100° C. and at a pressure sufficient to maintain the system in the liquid phase with an adsorbent composition comprising at least one crystalline aluminosilicate zeolite of modified Type Y having a cation site concentration of from about 40 to about 10 equivalents per mole unit cell and a face-centered cubic unit cell having an $a_o$ for the decationized form of from 24.3 to 24.6 Å in which the zeolite cations are more than 50% barium, whereby lactulose is selectively adsorbed thereon; removing the non-adsorbed portion of said mixture from contact with the zeolite adsorbent; and desorbing the lactulose therefrom by contacting said adsorbent with a desorbing agent and removing the desorbed lactulose.

* * * * *